(12) United States Patent
Toledano et al.

(10) Patent No.: US 11,628,155 B2
(45) Date of Patent: Apr. 18, 2023

(54) METHOD FOR THERAPEUTIC TREATMENT OF ROSACEA

(71) Applicant: Sol-Gel Technologies Ltd., Ness Ziona (IL)

(72) Inventors: Ofer Toledano, Kfar Saba (IL); Ori Nov, Tarum (IL)

(73) Assignee: SOL-GEL TECHNOLOGIES LTD., Ness Ziona (IL)

( * ) Notice: Subject to any disclaimer, the term of this patent is extended or adjusted under 35 U.S.C. 154(b) by 312 days.

(21) Appl. No.: 16/794,692

(22) Filed: Feb. 19, 2020

(65) Prior Publication Data
US 2020/0261396 A1 Aug. 20, 2020

Related U.S. Application Data

(60) Provisional application No. 62/977,974, filed on Feb. 18, 2020, provisional application No. 62/977,952, (Continued)

(51) Int. Cl.
*A61K 31/327* (2006.01)
*A61P 17/10* (2006.01)
(Continued)

(52) U.S. Cl.
CPC ......... *A61K 31/327* (2013.01); *A61K 9/0014* (2013.01); *A61K 9/06* (2013.01);
(Continued)

(58) Field of Classification Search
CPC ...... A61K 31/327; A61K 8/38; A61K 9/0014; A61K 9/06; A61K 9/10; A61K 9/107;
(Continued)

(56) References Cited

U.S. PATENT DOCUMENTS 9,107,844 B2 8/2015 Clark et al.
9,439,857 B2 9/2016 Tamarkin et al.
(Continued)

FOREIGN PATENT DOCUMENTS

DE 202011100767 U1 12/2011
WO 2008/057411 A1 5/2008
(Continued)

OTHER PUBLICATIONS

International Search Report and Written Opinion dated May 19, 2020 in International Patent Application No. PCT/US2020/18906, 19 pages.
(Continued)

*Primary Examiner* — Savitha M Rao
(74) *Attorney, Agent, or Firm* — Sheppard, Mullin, Richter & Hampton LLP

(57) ABSTRACT

A regimen and a pharmaceutical composition for the treatment of rosacea are described. The regimen includes topically applying to the skin of a subject in need of such treatment a pharmaceutical composition comprising about 1% w/w to about 10% w/w benzoyl peroxide as an active ingredient, and the pharmaceutically acceptable carrier or excipient, where the benzoyl peroxide is the only active ingredient in the pharmaceutical composition, and the pharmaceutical composition is a cream or an emulsion.

52 Claims, 2 Drawing Sheets

Related U.S. Application Data filed on Feb. 18, 2020, provisional application No. 62/972,896, filed on Feb. 11, 2020, provisional application No. 62/972,310, filed on Feb. 10, 2020, provisional application No. 62/960,384, filed on Jan. 13, 2020, provisional application No. 62/925,258, filed on Oct. 24, 2019, provisional application No. 62/871,286, filed on Jul. 8, 2019, provisional application No. 62/871,283, filed on Jul. 8, 2019, provisional application No. 62/807,368, filed on Feb. 19, 2019, provisional application No. 62/807,356, filed on Feb. 19, 2019.

(51) Int. Cl.
| | |
|---|---|
| A61K 9/00 | (2006.01) |
| A61K 9/06 | (2006.01) |
| A61K 9/107 | (2006.01) |
| A61P 17/00 | (2006.01) |
| A61K 9/50 | (2006.01) |
| A61K 9/10 | (2006.01) |

(52) U.S. Cl.
CPC .............. *A61K 9/10* (2013.01); *A61K 9/107* (2013.01); *A61K 9/50* (2013.01); *A61P 17/00* (2018.01); *A61P 17/10* (2018.01)

(58) Field of Classification Search
CPC . A61K 9/50; A61P 17/00; A61P 17/10; A61Q 19/00
See application file for complete search history.

(56) References Cited

U.S. PATENT DOCUMENTS

| | | | |
|---|---|---|---|
| 9,687,465 | B2 | 6/2017 | Sertchook et al. |
| 9,693,988 | B2 | 7/2017 | Chang et al. |
| 10,653,899 | B2 | 5/2020 | Toledano et al. |
| 10,933,046 | B2 | 3/2021 | Toledano et al. |
| 10,945,987 | B2 | 3/2021 | Toledano et al. |
| 2004/0171561 | A1 | 9/2004 | Popp |
| 2009/0306172 | A1 | 12/2009 | Chang et al. |
| 2010/0016443 | A1 | 1/2010 | Toledano et al. |
| 2010/0143285 | A1 | 6/2010 | Mallard et al. |
| 2011/0052515 | A1 | 3/2011 | Kaoukhov et al. |
| 2011/0262506 | A1 | 10/2011 | Toledano et al. |
| 2012/0064135 | A1 | 3/2012 | Levin et al. |
| 2013/0095185 | A1 | 4/2013 | Toledano et al. |
| 2014/0121188 | A1 | 5/2014 | Tamarkin et al. |
| 2014/0147396 | A1 | 5/2014 | Sertchook et al. |
| 2017/0216282 | A1 | 8/2017 | Dejovin et al. |
| 2017/0281571 | A1 | 10/2017 | Sertchook et al. |
| 2018/0147165 | A1 | 5/2018 | Sertchook et al. |
| 2020/0261397 | A1 | 8/2020 | Toledano et al. |
| 2020/0383927 | A1 | 12/2020 | Toledano et al. |
| 2020/0405665 | A1 | 12/2020 | Sertchook et al. |
| 2021/0000741 | A1 | 1/2021 | Shevachman et al. |
| 2021/0290985 | A1 | 9/2021 | Toledano et al. |

FOREIGN PATENT DOCUMENTS

| | | |
|---|---|---|
| WO | 2008/093346 A2 | 8/2009 |
| WO | 2011/049547 A1 | 4/2011 |
| WO | 2011/101868 A2 | 8/2011 |
| WO | 2014/083557 A1 | 6/2014 |

OTHER PUBLICATIONS

Matin, et al., "Benzoyl Peroxide"; Review from StatPearls Publishing, Treasure Island (FL), 4 pages (Feb. 6, 2019).
Wepierre, et al., "Distribution and dissociation of benzoyl peroxide in cutaneous tissue after application on skin in the hairless rat", International Journal of Cosmetic Science, vol. 8, pp. 97-104 (Jun. 1986).
Nacht, et al., "Benzoyl peroxide: Percutaneous penetration and metabolic disposition", Journal the American Academy of Dermatology, vol. 4, pp. 31-37 (Jan. 1981).
International Search Report and Written Opinion dated Jul. 15, 2020 in International Patent Application No. PCT/IB2020/00125, 16 pages.
International Search Report and Written Opinion dated Aug. 10, 2020 in International Patent Application No. PCT/IB2020/00118, 14 pages.
International Search Report and Written Opinion dated Aug. 12, 2020 in International Patent Application No. PCT/IB2020/00126, 19 pages.
International Search Report and Written Opinion dated Aug. 14, 2020 in International Patent Application No. PCT/IB2020/00123, 13 pages.
Montes, et al., "Topical Treatment of Acne Rosacea with Benzoyl Peroxide Acetone Gel," Therapeutics for the Clinician: New Reports on Treatment Modalities of Possible Interest to Patient-Caring Physicians, vol. 32, pp. 185-190 (1983).
Wilkin, et al., "Standard grading system for rosacea: Report of the National Rosacea Society Expert Committee on the Classification and Staging of Rosacea", Journal of the American Academy of Dermatology, vol. 50 (Jun. 2004), available at https://www.rosacea.org/physicians/grading-system-for-rosacea/view-online.
U.S. Non-Final Office Action dated May 28, 2020 in U.S. Appl. No. 16/794,809, 11 pages.
U.S. Non-Final Office Action dated Jul. 8, 2020 in U.S. Appl. No. 16/794,839, 9 pages.
Wollina, Uwe "Rosacea and rhinophyma in the elderly", Clinincs in Dermatology, vol. 29, pp. 61-68 (2011).
Oge, et al., "Rosacea: Diagnosis and Treatment," American Family Physician, vol. 92, pp. 187-198 (2015).
Gül, et al. "A case of granulomatous rosacea successfully treated with pimecrolimus cream", Journal of Dermatological Treatment, vol. 19, pp. 313-315 (2008).
Wester, et al., "Controlled release of benzoyl peroxide from a porous microsphere polymeric system can reduce topical irritancy", Journal of the American Academy of Dermatology, vol. 24, pp. 720-726 (1991).
Sawleshwarkar, et al., "Multicenter study to evaluate efficacy and irritation potential of benzoyl peroxide 4% cream in hydrophase base (Brevoxyl) in acne vulgaris," Indian Journal of Dermatology, Venereology and Leprology, vol. 69, pp. 19-22 (2003).
Breneman, et al., "Double-blind, randomized, vehicle-controlled clinical trial of once-daily benzoyl peroxide/clindamycin topical gel in the treatment of patients with moderate to severe rosacea," International Journal of Dermatology, vol. 43, pp. 381-387 (2004).
Gold, et al., p. 161 "Use of Benzoyl Peroxide/Clindamycin gel in the once daily treatment of moderate rosacea," Journal of the American Academy of Dermatology, vol. 52, suppl. p. 25 (2005).
Leyden, et al., p. 53 "Blinded photographic review for a double blind, multicenter, placebo-controlled study comparing Benzoyl Peroxide/Clindamycin and placebo for the treatment of rosacea," Journal of the American Academy of Dermatology, vol. 52, suppl. p. 14 (2004).
Goldgar, et al., "Treatment Options for Acne Rosacea," American Family Physician, vol. 80, pp. 461-468 (2009).
Crawford, et al., "Rosacea: I. Etiology, pathogenesis, and subtype classification," Journal of the American Academy of Dermatology, vol. 51, pp. 327-341 (2004).
McGregor, et al., "A Review of the Current Modalities of the Treatment of Papulopustular Rosacea," Dermatologic Clinics, vol. 36, 16 pages (2017).
Feaster, et al., "Clinical effectiveness of novel rosacea therapies," Current Opinion in Pharmacology, vol. 46, pp. 14-18 (2019).
Del Rosso, et al., "Update on the Management of Rosacea from the American Acne & Rosacea Society (AARS)", The Journal of Clinical & Aesthetic Dermatology, vol. 12, pp. 17-24 (2019).
James, et al., "Rosacea", Andrews' Diseases of the Skin: Clinical Dermatology, 10th ed., Saunders Elsevier, pp. 239-248 (2005).
International Search Report and Written Opinion dated Aug. 28, 2020 in International Patent Application No. PCT/IB2020/00120, 15 pages.

(56) References Cited

OTHER PUBLICATIONS

U.S. Non-Final Office Action dated Jul. 7, 2020 in U.S. Appl. No. 16/794,734, 8 pages.
International Search Report and Written Opinion dated Oct. 5, 2020 in International Patent Application No. PCT/IB2020/00119, 25 pages.
Nicholson, K. et al., "A pilot quality-of-life instrument for acne rosacea", Journal of the American Aademy of Dermatology, vol. 57, No. 2, 213-221.(2007).
Non-Final Office Action dated Apr. 11, 2022 in U.S. Appl. No. 16/794,923, 28 pages.

METHOD FOR THERAPEUTIC TREATMENT OF ROSACEA

CROSS-REFERENCE TO RELATED APPLICATIONS

This application claims priority under 35 U.S.C. § 119(e) from U.S. Provisional Application No. 62/977,974, filed Feb. 18, 2020, U.S. Provisional Application No. 62/977,952, filed Feb. 18, 2020, U.S. Provisional Application No. 62/972,896, filed Feb. 11, 2020, U.S. Provisional Application No. 62/972,310, filed Feb. 10, 2020, U.S. Provisional Application No. 62/960,384, filed Jan. 13, 2020, U.S. Provisional Application No. 62/925,258, filed Oct. 24, 2019, U.S. Provisional 62/871,286, filed Jul. 8, 2019, U.S. Provisional 62/871,283, filed Jul. 8, 2019, U.S. Provisional 62/807,356, filed Feb. 19, 2019, and U.S. Provisional 62/807,368, filed Feb. 19, 2019, the contents of which are incorporated in their entirety as if fully set forth herein.

TECHNICAL FIELD

This application relates to methods and compositions for the therapeutic treatment of skin conditions and afflictions, such as rosacea, and symptoms and considerations associated therewith, including topically applying to the skin of a subject in need of said treatment a pharmaceutical composition comprising benzoyl peroxide having high skin permeation and penetration, preferably in the upper layers of the skin.

BACKGROUND

Rosacea is a chronic disease of inflammatory dermatitis that mainly affects the median part of the face and the eyelids of certain adults. It is characterized by telangiectatic erythema, dryness of the skin, papules and pustules. Conventionally, rosacea develops in adults from the ages of 30 to 50, and more frequently affects women, although the condition is generally more severe in men. Rosacea is a primitively vascular condition whose inflammatory stage lacks the cysts and comedones characteristic of common acne.

Factors that have been described as possibly contributing towards the development of rosacea include, for example: the presence of parasites such as the *Demodex folliculorum*; the presence of bacteria such as *Helicobacter pylori* (a bacterium associated with gastrointestinal disorders); hormonal factors (such as endocrine factors); climatic and immunological factors; and so forth.

Rosacea develops in four stages over several years, in spasms aggravated by variations in temperature, alcohol, spices, exposure to sunlight and stress. The various stages of the disease are:

Stage 1 (stage of erythema episodes): the patients have erythrosis spasms due to the sudden dilation of the arterioles of the face, which then take on a congestive, red appearance. These spasms are caused by emotions, meals and temperature changes.

Stage 2 (stage of couperosis, i.e., of permanent erythema with telangiectasia): certain patients also have oedema on the cheeks and the forehead.

Stage 3 (inflammatory stage, papulopustular rosacea): patients exhibit appearance of inflammatory papules and pustules, but without affecting the sebaceous follicles, and thus, does not include cysts and comedones.

Stage 4 (rhinophyma stage): this late phase essentially affects men. The patients have a bumpy, voluminous red nose with sebaceous hyperplasia and fibrous reordering of the connective tissue.

Typical treatment of rosacea includes oral or topical administration of antibiotics such as tetracyclines, salicylic acid, anti-fungal agents, steroids, metronidazole (an antibacterial agent) and isotretinoin, or treatment with anti-infectious agents such as azelaic acid.

The skin of patients suffering from signs and symptoms of rosacea is generally dry and sensitive, and requires the use of emollients (like silicon oil, and fatty alcohols) and humectants (like glycerin or propylene glycol) as a component of the vehicle used to deliver the appropriate drug during treatment of said signs and symptoms. Most emollients are water insoluble oils and the use of surfactants is needed in order to emulsify them in the vehicle. In general, creams contain both emulsified emollients and humectants while gels usually contain only emollients. Therefore, in a preferred formulation, it may be beneficial to include emollients and humectants in a cream to treat dry rosacea skin.

Papulopustular pathogens, such as bacteria and/or mites, are present on the surface of the skin and in its upper layers. Therefore, in the treatment of papulopustular rosacea, the vehicle needs to be designed to keep a higher percentage of the active ingredient at the upper layers of the skin and reduce the amount of API into the deeper layers of the skin.

SUMMARY

An exemplary embodiment of this application is a regimen for the therapeutic treatment of rosacea, the regimen comprising topically applying to the skin of a subject in need of said treatment a pharmaceutical composition, the pharmaceutical composition comprising about 1.0% w/w to about 10% w/w benzoyl peroxide as an active ingredient, and a pharmaceutically acceptable carrier or excipient, wherein the benzoyl peroxide is the only active ingredient in said pharmaceutical composition, wherein said pharmaceutical composition is a cream or an emulsion.

Another exemplary embodiment of this application is a pharmaceutical composition for use as a medicament in the treatment of rosacea, said pharmaceutical composition comprising from about 1.0% w/w to about 10% w/w benzoyl peroxide as an active ingredient, and a pharmaceutically acceptable carrier or excipient, wherein the benzoyl peroxide is the only active ingredient in said pharmaceutical composition, wherein said pharmaceutical composition is a cream or an emulsion.

Another exemplary embodiment of this application is the use of a pharmaceutical composition for providing therapeutic treatment of rosacea, said pharmaceutical composition comprising from about 1% w/w to about 10% w/w benzoyl peroxide as an active ingredient, and a pharmaceutically acceptable carrier or excipient, wherein the benzoyl peroxide is the only active ingredient in said pharmaceutical composition, wherein said pharmaceutical composition is a cream or an emulsion.

In another exemplary embodiment, the total amount of benzoic acid in the skin of the subject after treatment with the pharmaceutical composition is less than 11,000 ng. In certain embodiments, the total amount of benzoic acid in the skin of the subject after treatment with said pharmaceutical composition ranges from about 4,000 ng to about 6,000 ng, more preferably ranges from about 4,500 ng to about 5,500 ng.

In another exemplary embodiment, the amount of benzoic acid in the stratum corneum and the epidermis of the skin of the subject after treatment with said pharmaceutical composition is higher than the amount of benzoic acid in the dermis of the skin of the subject after treatment with said pharmaceutical composition.

In other exemplary embodiments, the benzoyl peroxide is the sole active ingredient administered to the subject during the duration of the regimen.

In other exemplary embodiments, the pharmaceutical composition comprises about 2.5% w/w to about 10% w/w of benzoyl peroxide.

In other exemplary embodiments, the pharmaceutical composition comprises about 5% w/w of benzoyl peroxide.

In other exemplary embodiments, the benzoyl peroxide is selected from a solid, solution or suspension form.

In other exemplary embodiments, the rosacea is any of erythematotelengietatic rosacea, papulopustular rosacea, phymatous rosacea or ocular rosacea.

In other exemplary embodiments, said pharmaceutical composition is an extended release formulation.

In other exemplary embodiments, the extended-release effect is obtained by encapsulation, microencapsulation, microspheres or coating.

In other exemplary embodiments, the benzoyl peroxide is encapsulated or microencapsulated.

In other exemplary embodiments, the benzoyl peroxide is included in a microsphere or a coating.

In other exemplary embodiments, irritation observed on the skin of the subject after treatment with said pharmaceutical composition remains constant over time.

Details of other exemplary embodiments of the present disclosure will be included in the following detailed description and the accompanying figures. It is appreciated that certain features of the exemplary embodiments described in this application, which are, for clarity, described in the context of separate embodiments, can also be provided in combination in a single embodiment.

BRIEF DESCRIPTION OF THE DRAWINGS

In order to understand the disclosure and to see how it can be carried out in practice, embodiments will now be described, by way of non-limiting examples only, with reference to the accompanying drawings, in which.

DETAILED DESCRIPTION

Figure 1:
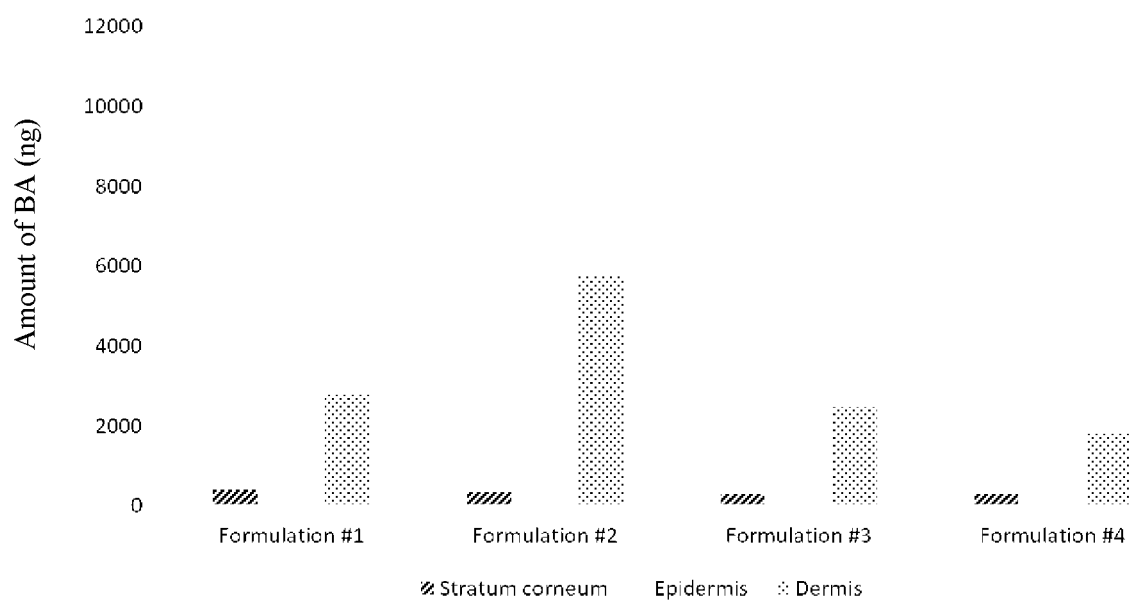
FIG. 1 is a graphical representation of mean cumulative amount of benzoic acid (ng), the conversion product of BPO, recovered from epidermis and dermis 24 h post-application of 4 formulations, in each of the stratum corneum, epidermis and dermis layers of the skin.

Multiple studies have been directed to the treatment of rosacea using a pharmaceutical or dermatological active agent such as metronidazole, azelaic acid, sulfacetamide, brimonidine, ivermectin, permethrin and clindamycin, and with doxycycline, which is identified as the only FDA-approved treatment for rosacea (Oge et al., "Rosacea: Diagnosis and Treatment," American Family Physician, v. 92(3), pp. 187-198 (2015); Gul et al., "A case of granulomatous rosacea successfully treated with pimecrolimus cream," J. Derm. Treatment, 19, 313-315 (2008)).

Benzoyl peroxide (BPO) is generally identified as an anti-acne agent, used alone (U.S. Pat. No. 9,439,857; Wester et al., "Controlled release of benzoyl peroxide from a porous microsphere polymeric system can reduce topical irritancy," J. Am. Acad. Derma. 24, 720-726 (1991); Sawleshwarkar, "Multicenter study to evaluate efficacy and irritation potential of benzoyl peroxide 4% cream in hydrophase base (Brevoxyl) in acne vulgaris," Ind. J. Derm. Vener. Lepro., 69(1), 19-22 (2003)) or in combination with a primary active such as avermectin (U.S. 2011/0052515).

One such study includes a therapeutic regimen involving treatment of acne rosacea in a group of patients in need of such treatment with 5% BPO-acetone gel for four weeks, followed by treatment of the same group of patients with 10% BPO-acetone gel for an additional four weeks. (Montes et al., "Topical Treatment of Acne Rosacea with Benzoyl Peroxide Acetone Gel," Therapeutics for the Clinician: New Reports on Treatment Modalities of Possible Interest to Patient-Caring Physicians, 32, 185-190 (1983)). The Montes study showed a significantly better response during the five to eight weeks of treatment with 10% BPO-acetone gel compared to the first four weeks of treatment with 5% BPO-acetone gel. Moreover, although Montes 1983 claims success in the treatment of rosacea using a BPO-acetone gel, 25% of the patients in the study showed no improvement and 40% of the patients developed an irritation. Additionally, this study required increasing the amount of BPO administered to the patients from 5% to 10% after week four. The results of the Montes 1983 study make it clear that BPO would not be suitable for regular use in the treatment of rosacea, especially as a first line treatment of rosacea.

Other studies show that, when used in the treatment of rosacea, BPO is generally combined with a primary active agent such as clindamycin (Breneman et al., "Double-blind, randomized, vehicle-controlled clinical trial of once-daily benzoyl peroxide/clindamycin topical gel in the treatment of patients with severe rosacea," Int. J. Derm., 43, 381-387 (2004); Gold et al., "Use of Benzoyl Peroxide/Clindamycin gel in the once daily treatment of moderate rosacea," J. Amer. Acad. Dermat., 52(3), sup., P25 (2004); Leyden et al., "Blind photographic review for a double blind, multicenter, placebo-controlled study comparing Benzoyl Peroxide/Clindamycin and placebo for the treatment of rosacea," J Amer. Acad. Dermat., 52(3), sup., P14 (2004); Goldgar et al., "Treatment Options for Acne Rosacea," J Amer. Fam. Physician, 80(5), 461-468 (2009)).

BPO is generally identified as only a possible second-line treatment of rosacea following the use of another, different active. (Oge 2015, Table 5; Goldgar 2009, "Key Recommendations for Practice"). When BPO was used as the sole active agent for the treatment of rosacea, lesions were found to be unresponsive. (Gul 2008).

These previous rosacea treatments with BPO alone or in combination with other agents, have been shown to have several drawbacks such as irritation and intolerance phenomena, especially when they are administered for a prolonged period. (Crawford et al., "Rosacea: I. Etiology, pathogenesis, and subtype classification," J. Am. Acad. Dermatol., 51, 327-341 (2004)). These treatments are only suppressive and not curative, acting especially on the pustulous spasms occurring during the inflammatory stage.

Such drawbacks associated with the treatment of rosacea involving the use of BPO result in exclusion of BPO from standard rosacea treatment methods. For example, "A Review of the Current Modalities for the Treatment of Papulopustular Rosacea" identifies metronidazole, ivermectin and azelaic acid as topical therapies that were proven effective for the treatment of rosacea. (McGregor et al., "A Review of the Current Modalities of the Treatment of Papulopustular Rosacea," *Dermatol. Clin.* (2017)). While McGregor 2017 mentions alternate therapies, such as sodium sulfacetanide/sulfur cream, clindamycin, tretinoin, calcineurin inhibitors and oral tretinoin, that may have some effectiveness in the treatment of rosacea, notably, *McGregor 2017* does not include, or even mention, BPO in the long list of possible treatment therapies described therein. The absence of BPO as a known treatment for rosacea is also evident in other studies. (Feaster et al., "Clinical effectiveness of novel rosacea therapies," *Current Op. Pharmacol.,* 46, 14-18 (2019); Del Rosso et al., "Update on the Management of Rosacea from the American Acne & Rosacea Society (AARS); *J. Clinical & Aesthetic Dermat.,* 12 (6), 17-24 (2019)). The absence of BPO as a recognized first-line treatment for rosacea is especially evident in *Del Rosso*, which is a well-known and respected authority on the treatment of rosacea. The AARS review lists the Society's recommendation for rosacea treatment, including topical metronidazole, topical azelaic acid, oral tetracyclines, ivermectin, topical alpha agonists, and oral isotretinoin, as well as "alternative therapies," such as sulfacetamide/sulfur, calcineurin inhibitors, retinoids, and permethrin. (See e.g., Table 1 of the AARS review.) BPO is not mentioned in the AARS review either as a leading, or even an alternative, therapeutic agent for the treatment of rosacea.

Considering the chronic nature of rosacea, there is a need for long-term treatment of the disease, its symptoms and associated conditions, in a safe and effective manner. Thus, there exists a need for compositions that have long-term, and improved, efficacy in the treatment of rosacea, that impart greater tolerance to the active principles and that reduce, substantially minimize or do not have the side effects described in the prior art. There also exists a need for long-term, prolonged treatment of rosacea without any accompanying adverse effects.

Benzoyl peroxide is highly unstable on the skin and decomposes rapidly to its only metabolite, benzoic acid. Therefore, levels of benzoic acid in the skin layers are good indicator to presence of benzoyl peroxide in these layers.

Additionally, as discussed above, in the treatment of papulopustular rosacea, the vehicle needs to be designed to keep a higher percentage of the active ingredient available at and/or within the upper layers of the skin and reduce the amount of API delivered to, absorbed in, and/or penetrated into the deeper layers of the skin or penetrate the skin. The effect of surfactants on the enhancement of drug permeation through skin has been well reviewed. Research in this area has proved the usefulness of surfactants, such as chemical penetration enhancers in transdermal drug delivery. In many instances, surfactants have been found to be more effective than other enhancers. (Som et al., "Status of surfactants as penetration enhancers in transdermal drug delivery," *J Pharm Bioallied Sci.,* 4(1), 2-9 (2012).) Nonionic surfactants, which are a safe class of enhancers, offer a means of enhancing drug permeation through the skin. For example, Nokhodchi et. al. ("The enhancement effect of surfactants on the penetration of lorazepam through rat skin.," *Int J Pharm.,* 250, 359-69 (2003)) reported two possible mechanisms by which the rate of transport is enhanced using nonionic surfactants—first, the surfactant may penetrate into the intercellular regions of the stratum corneum, increase fluidity and eventually solubilize and extract lipid components; and second, penetration of surfactant into the intercellular matrix followed by interaction and binding with keratin filaments may result in a disruption within the corneocyte. Furthermore, non-ionic surfactants are able to emulsify sebum, thereby enhancing the thermodynamic coefficient of drugs and allowing it to penetrate into the cells more effectively (Smith et al. Percutaneous penetration enhancer. 2nd ed. Boca Raton: Taylor and Francis (2005).)

Studies of the effect of carrier/vehicle on skin penetration have also been carried out. Occlusive and lipophilic vehicles such as paraffin, fats and oils reduce water loss, increase the moisture content in the skin and thus promote drug penetration. (Flate et al., "In vitro skin models as a tool in optimization of drug formulation," *European Journal of Pharmaceutical Sciences,* 75, 10-24 (2015); Stahl et al., "The effect of formulation vehicles on the in vitro percutaneous permeation of ibuprofen," *BMC Pharmacology,* 11(12), 1-5 (2011).)

The effect of different 5% ibuprofen containing formulations (Ibutop® cream, Ibutop® gel, and ibuprofen solution in phosphate buffered saline) on the in vitro-percutaneous permeation of ibuprofen through skin emphasized the importance of the formulation on percutaneous permeation and skin reservoir has also been studied (Stahl 2011). Although ibuprofen permeation out of the gel increases rapidly within the first four hours, the cream produced the highest ibuprofen delivery through the skin within 28 hours, followed by the solution and the gel.

BPO cream contains, nonionic surfactants, cyclomethicone, cetyl alcohol and glycerin. BPO gel is surfactants and oil free and contains only glycerin. Based on previous studies, BPO cream should have higher skin penetration, similar to the findings on ibuprofen. Surprisingly, it was found in an ex vivo skin penetration study on human skin that both encapsulated and non-encapsulated BPO creams have lower skin penetration than encapsulated and non-encapsulated BPO gels.

Advantages and features of the present disclosure, and methods for accomplishing the same will be more clearly understood from exemplary embodiments described below with reference to any accompanying figures. However, the present disclosure is not limited to the following exemplary embodiments and can be implemented in various different forms. The exemplary embodiments are provided only to provide sufficient disclosure of the present discoveries and to fully provide a person having ordinary skill in the art to which the present disclosure pertains within the technical field, and the present disclosure will be defined by any appended claims and combinations thereof.

As used herein, like reference numerals generally denote like elements throughout the present specification. Further, in the following description, a detailed explanation of well-known related technologies can be omitted to avoid unnecessarily obscuring the subject matter of the present disclosure.

As used herein, terms such as "including" and "having" are generally intended to allow other components to be included unless the terms are used in conjunction with the term "only."

As used herein, the term "topical use" is meant to encompass the topical administration of an exemplary composition by formulating said composition in any way known in the art, or in formulations disclosed herein, which are compatible with the skin, mucous membranes and/or the integuments.

As used herein, the term "treating" or "treatment" includes curing a condition, treating a condition, preventing or substantially preventing a condition, treating symptoms of a condition, curing symptoms of a condition, ameliorating, reducing and/or minimizing symptoms of a condition, treating effects of a condition, ameliorating, reducing and/or minimizing effects of a condition, and preventing and/or substantially preventing results of a condition, As used herein, the term "first-line therapy" or "first-line treatment" means a therapy or treatment for which its label does not include a requirement or recommendation that said therapy or treatment should be used only after other therapies or treatments were shown to be unsatisfactory or unsuccessful. It can also include a therapy and/or treatment wherein no other actives (beyond the main active) are administered to the individual subject in need.

As used herein, the term "success rate" corresponds to of the sum of the number of subjects achieving "clear" or "almost clear" skin on the investor global assessment (IGA) scale after treatment with the pharmaceutical composition, which can also be represented as a percentage of study subjects.

As used herein, the term "early onset" or "early onset of action" means achieving a desired result and/or effect at a point in time that is earlier or even much early than achieved using a vehicle or other, conventional treatment approach. For example, it can mean achieving a desired result and/or effect no later than about 8 weeks from initial treatment, preferably no later than about 4 weeks from initial treatment, and more preferably no later than about 2 weeks from initial treatment.

As used herein, the term "pharmaceutical composition" refers to a composition comprising one or more active ingredients with other components such as, for example, pharmaceutically acceptable ingredients and/or excipients. The purpose of a pharmaceutical composition is to facilitate administration of an active ingredient to a subject.

As used herein, the terms "pharmaceutically active agent" or "active agent" or "active pharmaceutical ingredient" are interchangeable and mean the ingredient is a pharmaceutical drug, which is biologically- and/or chemically-active and is regulatory-approved or approvable as such.

As used herein, the term "ingredient" refers to a pharmaceutically acceptable ingredient, which is included or is amenable to be included in The FDA's Inactive Ingredient (IIG) database. Inactive ingredients can sometimes exhibit some therapeutic effects, although they are not drugs.

As used herein, the term "adverse events values" refers to an average percentage of subjects that experience any adverse events associated with the treatment of rosacea with a composition described and/or claimed herein (usually on a surface of the skin of a subject treated with a composition described and/or claimed herein). A non-limiting list of such adverse events includes: irritation, dryness, scaling, itching purities, burning, stinging, combinations thereof and the like.

As used herein, the term "long-term" indicates prolonged use of a pharmaceutical ingredient for at least about 12 weeks or longer, at least about 40 weeks or longer, and more preferably at least about 52 weeks or longer, in a treatment regimen.

As used herein, the term "inflammatory lesion" refers to papules and pustules present on the skin of a patient, and does not include nodules and cysts.

As used herein, the term "papule" refers to a solid, elevated inflammatory lesion equal to or less than about 5 mm in diameter.

As used herein, the term "pustule" refers to an elevated inflammatory, pus-containing lesion equal to or less than about 5 mm in diameter.

As used herein, the term "nodule" and/or "cyst" refers to palpable solid inflammatory lesion, greater than about 5 mm in diameter. The nodule and/or cyst may have depth but does not necessarily include elevation.

As used herein, the term "high skin penetration" and/or "intradermal penetration" refers to a higher amount of the active ingredient delivered to, absorbed in and/or penetrated into the upper skin layers (e.g., stratum corneum and epidermis) compared to the amount of the active ingredient delivered to, absorbed in and/or penetrated into the deeper layers (e.g., dermis) of the skin or thorough the skin into the blood or receptor solution.

Whenever a numerical range is indicated herewith, it is meant to include any cited numeral (fractional or integral) within the indicated range. The phrases "ranging/ranges between" a first indicated number and a second indicated number and "ranging/ranges from" a first indicated number "to" a second indicated number are used herein interchangeable and are meant to include the first and second indicated numbers and all fractional and integral numerals therebetween.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "10 μm" is intended to mean "about 10 μm."

As used herein, numbers and/or numerical ranges preceded by the term "about" should not be considered to be limited to the recited range. Rather, numbers and/or numerical ranges preceded by the term "about" should be understood to include a range accepted by those skilled in the art for any given element in formations according to the subject invention.

As used herein, when a numerical value is preceded by the term "about," the term "about" is intended to indicate +/−10%.

As used herein, the singular form "a," "an" and "the" include plural references unless the context clearly dictates otherwise. For example, the term "a compound" or "at least one compound" can include a plurality of compounds, including combinations and/or mixtures thereof.

As used herein, the term "method" refers to manners, means, techniques and procedures for accomplishing a given task including, but not limited to, those manners, means, technical and procedures either known to, or readily developed from known manners, means, techniques and procedures by practitioners of the chemical, pharmacological, biological, biochemical and medical arts.

It is appreciated that certain features of the exemplary embodiments described herein, which are, for clarity, described in the context of separate embodiments, can also be provided in combination in a single embodiment. Conversely, various features of the exemplary embodiments, which are, for brevity, described in the context of a single embodiment, can also be provided separately or in any suitable sub-combination or as suitable in any other described embodiment. Certain features described in the context of various embodiments are not to be considered essential features of those embodiments, unless the embodiment is inoperative without those elements.

An exemplary embodiment of this application is a regimen for the therapeutic treatment of rosacea, the regimen comprising topically applying to the skin of a subject in need of said treatment a pharmaceutical composition, the pharmaceutical composition comprising about 1% w/w to about 10% w/w, preferably about 2.5% w/w to about 10% w/w, and more preferably, about 5% w/w benzoyl peroxide as an active ingredient, and a pharmaceutically acceptable carrier or excipient, wherein the benzoyl peroxide is the only active ingredient in said pharmaceutical composition, wherein said pharmaceutical composition is a cream or an emulsion.

An exemplary embodiment of this application is a regimen for the therapeutic treatment of rosacea, the regimen comprising topically applying to the skin of a subject in need of said treatment a pharmaceutical composition, the pharmaceutical composition comprising about 1% w/w to about 10% w/w, preferably about 2.5% w/w to about 10% w/w, and more preferably, about 5% w/w benzoyl peroxide as an active ingredient, and a pharmaceutically acceptable carrier or excipient, wherein the benzoyl peroxide is the only active ingredient in said pharmaceutical composition, wherein said pharmaceutical composition is a cream or an emulsion and wherein a total amount of benzoic acid in the skin of the subject after treatment with said pharmaceutical composition is less than 11,000 ng, preferably from about 4000 ng to about 6000 ng, from about 4250 ng to about 5750 ng, from about 4500 ng to about 5500 ng, from about 4750 ng to about 5250 ng.

Another exemplary embodiment of this application is a pharmaceutical composition for use as a medicament in the treatment of rosacea, said pharmaceutical composition comprising from about 1% w/w to about 10% w/w, preferably about 2.5% w/w to about 10% w/w, and more preferably, about 5% w/w benzoyl peroxide as an active ingredient, and a pharmaceutically acceptable carrier or excipient, wherein the benzoyl peroxide is the only active ingredient in said pharmaceutical composition, wherein said pharmaceutical composition is a cream or an emulsion.

Another exemplary embodiment of this application is a pharmaceutical composition for use as a medicament in the treatment of rosacea, said pharmaceutical composition comprising from about 1% w/w to about 10% w/w, preferably about 2.5% w/w to about 10% w/w, and more preferably, about 5% w/w benzoyl peroxide as an active ingredient, and a pharmaceutically acceptable carrier or excipient, wherein the benzoyl peroxide is the only active ingredient in said pharmaceutical composition, wherein said pharmaceutical composition is a cream or an emulsion, and wherein a total amount of benzoic acid in the skin of the subject after treatment with the pharmaceutical composition is less than 11,000 ng, preferably from about 4000 ng to about 6000 ng, from about 4250 ng to about 5750 ng, from about 4500 ng to about 5500 ng, from about 4750 ng to about 5250 ng.

Another exemplary embodiment of this application is the use of a pharmaceutical composition for providing therapeutic treatment of rosacea, said pharmaceutical composition comprising from about 1% w/w to about 10% w/w, preferably about 2.5% w/w to about 10% w/w, and more preferably, 5.0% w/w/benzoyl peroxide as an active ingredient, and a pharmaceutically acceptable carrier or excipient, wherein the benzoyl peroxide is the only active ingredient in said pharmaceutical composition, wherein said pharmaceutical composition is a cream or an emulsion.

Another exemplary embodiment of this application is the use of a pharmaceutical composition for providing therapeutic treatment of rosacea, said pharmaceutical composition comprising from about 1% w/w to about 10% w/w, preferably about 2.5% w/w to about 10% w/w, and more preferably, 5.0% w/w/benzoyl peroxide as an active ingredient, and a pharmaceutically acceptable carrier or excipient, wherein the benzoyl peroxide is the only active ingredient in said pharmaceutical composition, wherein said pharmaceutical composition is a cream or an emulsion, and wherein a total amount of benzoic acid in the skin of the subject after treatment with the pharmaceutical composition is less than 11,000 ng, preferably from about 4000 ng to about 6000 ng, from about 4250 ng to about 5750 ng, from about 4500 ng to about 5500 ng, from about 4750 ng to about 5250 ng.

In another exemplary embodiment, the amount of benzoic acid in the stratum corneum and the epidermis of the skin of the subject after treatment with said pharmaceutical composition is higher than the amount of benzoic acid in the dermis of the skin of the subject after treatment with said pharmaceutical composition.

In other exemplary embodiments, the benzoyl peroxide is the sole active ingredient administered to the subject during the duration of the regimen.

In other exemplary embodiments, the benzoyl peroxide is selected from a solid, solution or suspension form.

In other exemplary embodiments, the rosacea is any of erythematotelengietatic rosacea, papulopustular rosacea, phymatous rosacea or ocular rosacea.

In other exemplary embodiments, said pharmaceutical composition is an extended release formulation.

In other exemplary embodiments, the extended-release effect is obtained by encapsulation, microencapsulation, microspheres or coating.

In other exemplary embodiments, the benzoyl peroxide is encapsulated or microencapsulated.

In other exemplary embodiments, the benzoyl peroxide is included in a microsphere or a coating.

In other exemplary embodiments, irritation observed on the skin of the subject after treatment with said pharmaceutical composition remains constant over time.

In some further embodiments, the composition further comprises at least one non pharmaceutical active additive selected from the group consisting of chelating agents, antioxidants, sunscreens, preservatives, fillers, electrolytes, humectants, dyes, mineral or organic acids or bases, fragrances, essential oils, moisturizers, vitamins, essential fatty acids, sphingolipids, self-tanning compounds, calmatives and skin-protecting agents, pro-penetrating agents and gelling agents, or a mixture and/or combination thereof.

In other embodiments, the composition is formulated into a topically applicable, physiologically acceptable medium comprising of: (a) at least one member selected from the group consisting of water, alcohols, oils, fatty substances and waxes; and (b) at least one additive selected from the group consisting of chelating agents, antioxidants, sunscreens, preservatives, fillers, electrolytes, humectants, dyes, mineral acids, mineral bases, organic acids, organic bases, fragrances, essential oils, moisturizers, vitamins, essential fatty acids, sphingolipids, self-tanning compounds, calmatives, skin-protecting agents, pro-penetrating agents, gelling agents, emulsifiers, co-emulsifiers, and mixtures and/or combinations thereof.

In some embodiments the composition is formulated as an emulsion (including an oil-in-water emulsion, a water-in-oil emulsion, multiple emulsions and microemulsions). In other embodiments, the composition is formulated as a cream.

The compositions described in exemplary embodiments herein are pharmaceutical compositions, and especially dermatological compositions, which can be in any galenical form conventionally used for topical application. By addition of a fatty or oily phase, they can also be in the form of dispersions of the lotion or serum type, emulsions of liquid or semi-liquid consistency of the milk type obtained by dispersing a fatty phase in an aqueous phase (O/W) or conversely (W/O), or suspensions or emulsions of soft, semiliquid or solid consistency of the cream, gel or ointment type, or alternatively multiple emulsions (W/O/W or O/W/O), microemulsions, microcapsules, microparticles and/or vesicular dispersions of ionic and/or nonionic type, and/or wax/aqueous phase dispersions. These compositions are formulated according to the usual methods.

In further embodiments, the composition comprises, as a single pharmaceutical active agent, benzoyl peroxide in a solid form, for topical use in the treatment of rosacea, in an oil in water emulsion comprising a polyoxylstearate and a glycerylstearate. Various methods for the preparation of the BPO-containing compositions are described in U.S. Application Publication Nos. 2010/0016443, 2017/0281571 and 2018/0147165 and U.S. Pat. No. 9,687,465.

In some embodiments, the ratio of said polyoxylstearate to said glycerylstearate is in the range of about 0.1:10 to about 10:0.1.

In yet further embodiments, said polyoxylstearate is selected from the group consisting of Polyoxyl-8 stearate, Polyoxyl-20 stearate, Polyoxyl-40 stearate, Polyoxyl-100 stearate and combinations and/or mixtures thereof.

In further embodiments, said glycerylstearate is selected from the group consisting of glyceryl mono-stearate, glyceryl di-stearate and combinations and/or mixtures thereof.

In other embodiments, said polyoxylstearate in said composition is in the range of from about 0.1% w/w to about 30% w/w.

In further embodiments, the amount of said glycerylstearate in said composition is in the range of from about 0.1% w/w to about 30% w/w.

In other embodiments, said composition further comprises at least one fatty alcohol.

In other embodiments, said at least one fatty alcohol is selected from the group consisting of octyl alcohol, 2-ethyl hexanol. nonyl alcohol, decyl alcohol, undecanol, dodecyl alcohol, tridecyl alcohol, tetradecyl alcohol, pentadecyl alcohol, cetyl alcohol, palmitoleyl alcohol, heptadecyl alcohol, cetostearyl alcohol, stearyl alcohol, isostearyl alcohol, elaidyl alcohol, oleyl alcohol, linoleyl alcohol, elaidolinolenyl alcohol, ricinoleyl alcohol, nonadecyl alcohol, arachidyl alcohol, heneicosyl alcohol. behenyl alcohol, erucyl alcohol, lignoceryl alcohol, ceryl alcohol, montanyl alcohol, cluytyl alcohol, myricyl alcohol, melissyl alcohol, geddyl alcohol, cetearyl alcohol and combinations and/or mixtures thereof.

In further embodiments, the amount of said at least one fatty alcohol in said composition is in the range of from about 0.2% w/w to about 50% w/w.

In yet other embodiments, said composition further comprises a polyacrylic acid homopolymer or copolymer.

In other embodiments, said oil in said oil in water emulsion is selected from the group consisting of paraffin oil, isopropyl myristate, caprylic/capric triglyceride, squalane, squalene, almond oil, castor oil, olive oil, jojoba oil, sunflower oil, soybean oil, grape seed oil, dimethicone, cyclomethicone and combinations and/or mixtures thereof.

In further embodiments, said oil in present in the composition in an amount in the range of from about 0.05% w/w to about 50% w/w.

In some embodiments, said water in said oil in water emulsion further comprises at least one water soluble humectant.

In other embodiments, said at least one water soluble humectant is selected from the group consisting of propylene glycol, glycerin, polyethylene glycol-X and combinations and/or mixtures thereof, where X is in the range of from about 200 to about 10,000.

In some embodiments, the composition comprises said solid BPO in a controlled and/or slowed release drug delivery system. In further embodiments, said controlled and/or slowed release drug delivery system is an encapsulation in a microcapsule, wherein said solid BPO is embedded in said microcapsule. When referring to a "controlled and/or slowed release drug delivery system" it should be understood to relate to a delivery system (which in the present application is a topical delivery system) that enables the release of the pharmaceutical active agent in predetermined amounts over a specified period. In some embodiments, said system is a core-shell system of a microcapsule and/or a porous matrix structure, such as, for example, a microsponge. The term "embedded" should be understood to encompass an inert system that provides a barrier between the pharmaceutical active agent, i.e. BPO, and its surrounding environment in the composition. In some embodiments, said agent is entrapped and/or encapsulated in said controlled release system.

In some embodiments, said core of said microcapsule comprises or consists of said solid BPO.

In some further embodiments, said microcapsules are a core shell microcapsule. The shell comprises at least one inorganic polymer. In some other embodiments, said inorganic polymer of said shell is a metal oxide or semi-metal oxide shell (layer).

In some embodiments, said microcapsule comprises a metal oxide or semi-metal oxide coating or layer (shell) and a core comprising or consisting of solid BPO.

In some embodiments, said microcapsule comprises a metal oxide or semi-metal oxide coating or layer (shell) and a core comprising solid BPO is prepared by a process comprising the steps of:

(a) contacting a solid BPO particulate matter with an ionic additive and an aqueous medium to obtain a dispersion of said particulate matter having positive charges on its surface;

(b) subjecting the particulate matter to a coating procedure comprising precipitating a metal oxide salt onto the surface of the particulate matter to form a metal oxide layer thereon thereby to obtain particulate matter coated by a metal oxide coating layer;

(c) repeating step (b) at least 4 more times: and (d) aging said coating layer.

As used herein, the term "solid BPO particulate matter" refers to a solid BPO having solubility in water of less than about 1% w/w, typically less than about 0.5% and at times less than about 0.1% w/w at room temperature (about 20° C.). The "solid BPO particulate matter" constitutes the "core" of the particles obtained by the process. The solid BPO particulate matter, is, in some embodiments, in such a state of subdivision that it can be suspended in water, e.g., in the form of a finely-divided powder having a $D_{90}$ (see definition below), in some embodiments in the range of from about 0.3 to about 50 microns. Such a particulate matter can be readily suspended in an aqueous systems by stirring, with or without the aid of a surfactant.

The terms "solid BPO particulate matter" and "particulate matter" will be used interchangeably.

In the present application, the terms "layer", "coating" or "shell" and similar terms, refer to a layer of metal oxide or semi-metal oxide formed around a particle or particulate matter. The layer or coating need not always be complete or uniform and need not necessarily lead to complete coverage of the particulate matter or particle surface. It is appreciated that upon repetition of the coating steps as the coating process proceeds a more uniform coating and more complete coverage of the particulate matter is obtained.

The term "dispersion," as used herein, in step (a) of the process refers to a solid dispersion of the particulate matter in the aqueous medium. Step (a) of the process can further comprise reducing the particle size of the particulate matter to the desired particle size, for example, by milling or homogenization.

The core (i.e., solid, BPO particulate matter) can be of any shape, for example, rod-like, plate-like, ellipsoidal, cubic, spherical shape, combinations thereof and the like.

Reference to the size of particles will be made through their $D_{90}$, which means that about 90% of the particles have the stated dimension or less (measured by volume). Thus, for example, for spherical particles stated to have a diameter of about 10 micrometer ("microns"), this means that the particles have a $D_{90}$ of about 10 microns. The $D_{90}$ can be measured by laser diffraction. For particles having a shape other than spheres, the $D_{90}$ refers to the mean average of the diameter of a plurality of particles.

In the case of cores having a spherical shape, the $D_{90}$ can be in the range of from about 0.3 to 90 microns, in some embodiments from about 0.3 to about 50 microns, in some other embodiments from about 1 to about 50 microns, in some further embodiments from about 5 to about 30 microns. As used herein, the phrase "$D_{90}$ can be in the range of from about 0.3 microns to about 90 microns" means about 90% by volume of the particles (in this case the particle's core) can be less than or equal to a value in the range of from about 0.3 microns to about 90 microns.

For generally cubic-shaped cores or cores having a shape resembling that of a cube, the mean size of a side can be in the range of from about 0.3 to about 80 microns, in some embodiments from about 0.3 to about 40 microns, in some further embodiments from about 0.8 to about 40 microns, in some further embodiments from about 4 to about 15 microns.

For rod-like shaped, ellipsoidal-shaped and plate-like shaped cores, the largest dimension (that of the longest axis) is typically in the range of from about 10 to about 100 microns, in some embodiments from about 15 to about 50 microns; and the smallest dimension is typically in the range of from about 0.5 to about 20 microns, in some further embodiments from about 2 to about 10 microns.

As used herein, unless otherwise indicated, the term "particle" refers to the metal oxide or semi-metal oxide coated particulate matter.

It is appreciated that some of the particles obtained by the process can at times be formed from two or more original particles of the solid BPO particulate and can accordingly include at times more than one core, such cores being separated from each other by a metal oxide region.

The weight of the solid BPO particulate (core material) based on the total weight of the particle can be in the range of from about 99% w/w to about 50% w/w, in some embodiments in the range of from about 97% w/w to about 50% w/w. The core material can be in a crystalline form, amorphous form, or combination thereof. The core material can be a cosmetic, pharmaceutical or an agrochemical active ingredient.

EXEMPLARY EMBODIMENTS

BPO-containing compositions were prepared following the various preparation methods described in U.S. Application Publication Nos. 2010/0016443, 2017/0281571 and 2018/0147165 and U.S. Pat. No. 9,687,465, the contents of which are incorporated herein, by reference, in their entirety.

Description: The aim of this study was to perform in vitro permeation and penetration testing on BPO-containing formulations used to treat rosacea. The study objectives were achieved via implementation of an HPLC analytical method and a pilot in vitro skin permeation and penetration experiments using four different BPO-containing formulations, which are described in Tables 1 to 4 below:

TABLE 1

| Components of Formulation #1 (5% E-BPO Gel) | % w/w |
|---|---|
| E-BPO 15% Suspension | 33.33 |
| Carbopol 980 | 1.2 |
| Tromethamine 30% Solution | pH adjustment |
| EDTA Disodium Salt | 0.1 |
| Glycerin 99.5% | 5.0 |
| Phenoxyethanol | 0.1 |
| Purified water or higher grade | Up to 100 |

TABLE 2

| Components of Formulation #2 (5% BPO Gel) | % w/w |
|---|---|
| BPO 75% | 6.7 |
| Placebo for E-BPO 15% Suspension | 27.78 |
| Carbopol 980 | 1.2 |
| Tromethamine 30% Solution | pH adjustment |
| EDTA Disodium Salt | 0.1 |
| Glycerin 99.5% | 5.0 |
| Phenoxyethanol | 0.1 |
| Purified water or higher grade | Up to 100 |

TABLE 3

| Components of Formulation #3 (5% E-BPO Cream) | % w/w |
|---|---|
| E-BPO, 15% Suspension | 33.33 |
| Polyoxyl 100 stearate | 2.0 |
| Cetyl alcohol | 3.0 |
| Cyclomethicone 5-NF | 4.0 |
| Glyceryl Mono- and Di-stearate | 3.0 |
| Hydrochloric Acid 10% | pH adjustment |
| Citric Acid, anhydrous | 0.4 |
| Sodium Hydroxide Pellets | pH adjustment |
| EDTA Disodium Salt | 0.1 |
| Glycerin 99.5% | 4.0 |
| Phenoxymethanol | 0.5 |
| Purified water or higher grade | Up to 100 |

TABLE 4

| Components of Formulation #4 (5% BPO Cream) | % w/w |
|---|---|
| BPO 75% | 6.7 |
| Placebo for E-BPO 15% Suspension | 27.8 |
| Polyoxyl 100 stearate | 2.0 |
| Cetyl alcohol | 3.0 |
| Cyclomethicone 5-NF | 4.0 |
| Glyceryl Mono- and Di-stearate | 3.0 |
| Hydrochloric Acid 10% | pH adjustment |
| Citric Acid, anhydrous | 0.4 |
| Sodium Hydroxide Pellets | pH adjustment |
| EDTA Disodium Salt | 0.1 |
| Glycerin 99.5% | 4.0 |
| Phenoxymethanol | 0.5 |
| Purified water or higher grade | Up to 100 |

Pilot IVPT Study Design:

Human skin, freshly excised from one skin donor was mounted between the donor and receptor compartment of the diffusion cell (with an exposed dosing surface area of ~0.6 cm² for each replicate). The skin was dosed with ca. 12 µL of each of Formulations 1 to 4 to achieve a dose of ~20 µL/cm². Skin was also mounted in a blank cell to which no formulation was applied. A receptor solution stir rate of 600 rpm was employed, and 0.2 mL of receptor solution was sampled at approximately about 1 hour, about 2 hours, about 4 hours, about 6 hours, about 8 hours and about 24 hours. Receptor solution was analyzed using a single HPLC analytical method for both benzoyl peroxide and conversion product, benzoic acid.

After about 24 hours, the residual formulation was removed from the surface of the skin and the skin surface was tape stripped up to 5 times to remove residual formulation and the top of the skin surface layers (stratum corneum). The epidermis was then heat-separated from the dermis by placing the skin into an incubator at 60° C. for 2 min, followed by manual separation. The amount of benzoyl peroxide, and its metabolite benzoic acid, delivered to the stratum corneum, epidermis, and dermis was then determined by HPLC.

Figure 2:
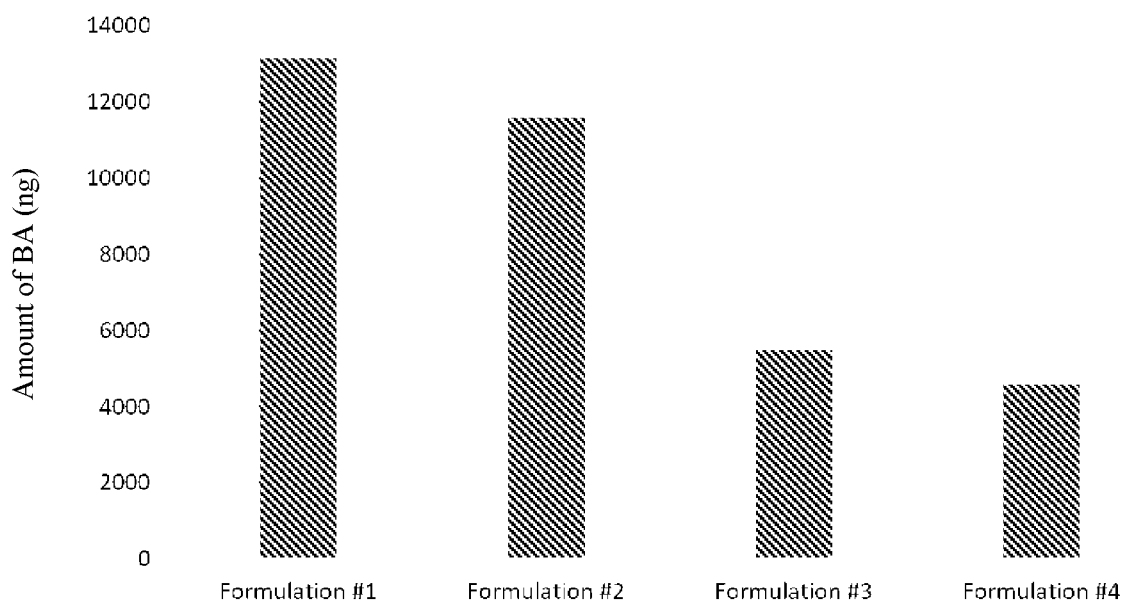
FIG. 2 is a graphical representation of the total amount (ng) of the benzoic acid that permeates the various layers of the skin.

Penetration and Permeation Results:

The mean amounts of benzoic acid (BA) (ng) recovered from the stratum corneum, epidermis and dermis after 24 h following application of the four formulations described above are shown in Table 5 and FIG. 1, while the total amount of benzoic acid (ng) recovered from the skin for each formulation is shown in Table 6 and FIG. 2. Samples below the limit of quantitation were set to a value of the limit of quantitation (100 ng).

TABLE 5

| Formulation | Amount of BA in the Stratum corneum (ng) | | | | Amount of BA in the Epidermis (ng) | | | | Amount of BA in the Dermis (ng) | | | |
| --- | --- | --- | --- | --- | --- | --- | --- | --- | --- | --- | --- | --- |
| | N | Mean | Std. Dev. | Std. Error | N | Mean | Std. Dev. | Std. Error | N | Mean | Std. Dev. | Std. Error |
| #1 | 5 | 348 | 74 | 33 | 5 | 5472 | 3805 | 1702 | 5 | 5771 | 1768 | 791 |
| #2 | 5 | 393 | 79 | 35 | 4 | 9991 | 560 | 280 | 5 | 2762 | 678 | 303 |
| #3 | 5 | 300 | 0 | 0 | 4 | 2464 | 280 | 140 | 5 | 1798 | 131 | 59 |
| #4 | 4 | 300 | 0 | 0 | 4 | 2712 | 246 | 123 | 5 | 2479 | 1516 | 678 |

TABLE 6

| | Total amount of BA in the skin (ng) |
| --- | --- |
| Formulation #1 | 11591 |
| Formulation #2 | 13146 |
| Formulation #3 | 4562 |
| Formulation #4 | 5491 |

Figure 3:
FIG. 3 is a photograph of the irritation observed on the skin after treatment with various BPO formulations.

Additionally, the mean cumulative amount of benzoic acid (ng/cm²) recovered from the receptor solution (RC), stratum corneum (SC), epidermis, and dermis at 24 h post-application of the four formulations is shown in FIG. 3. Bars represent the cumulative amount of benzoyl peroxide and benzoic acid from five replicates and one donor (n=4-5). Error bars represent standard error of the mean.

Skin Irritation Tests:

Enhancing penetration of BPO into the deep layers of the skin may cause skin irritation. Two different mixtures of BPO cream with a penetration enhancer transcutol, and humectant IPM were prepared by combining 5% E-BPO in a 120 ml polypropylene until a homogenous mixture was obtained. A third sample with water (without a penetrating agent) was used as a reference. The three mixtures have the following compositions:

Mixture #1: 45 g 5% E-BPO cream with 5 g water;
Mixture #2: 45 g 5% E-BPO cream with 5 g Transcutol (penetration enhancer);
Mixture #3: 45 g 5% E-BPO cream with 5 g Isopropyl myristate.

The amount of sample mixture in each patch was about 0.11 g to about 0.15 g, and all samples were prepared in duplicate. The samples were applied on the skin of a person and kept under occlusion for 6 hrs. After 6 hours the patch was removed and the skin was cleaned. Irritation was developed 2 h after the removal of the patch and remained constant for 48 h.

Irritation from the various samples was evaluated on a 0-3 scale as shown in Table 7 below. FIG. 3 is a photograph of the irritation observed on the skin.

TABLE 7

| | Mixture #1 | Mixture #2 | Mixture #3 |
| --- | --- | --- | --- |
| FIG. 3 (sample) | 0.5 | 2.0 | 0.0 |
| FIG. 3 (duplicate) | 0.0 | 2.0 | 0.5 |

The results show that transcutol as a skin penetrating agent caused moderate skin irritation. The skin irritation coming from the reference and the sample with the IPM was negligible. It is clear that increasing skin penetration causes skin irritation, therefore the formulations should be designed to avoid penetration of BPO into the deep layers of skin as shown in the present invention.

As shown by the results of Table 6 and FIG. 2, E-BPO gel (Formulation #1) and BPO Gel (Formulation #2) have a high amount of skin penetration and permeation compared to E-BPO Cream (Formulation #3) and BPO Cream (Formulation #4). However, as shown in Table 5 and FIG. 1, a significantly higher percentage of the active ingredient (BPO or encapsulated BPO) is available at the upper layers (stratum corneum and epidermis) of the skin for the cream compositions, which reduces the amount of API present in the deeper layers (dermis) of the skin. As discussed above, this is a desired level of skin penetration for the treatment of papulopustular rosacea. Additionally, any skin irritation observed after treating with the BPO formulations remains constant after about 2 hours. Accordingly, the BPO cream and encapsulated BPO cream have unexpectedly superior properties in the treatment of papulopustular rosacea.

Although the exemplary embodiments of the present disclosure have been described in detail with reference to the accompanying examples and drawings, the present disclosure is not limited thereto and can be embodied in many different forms without departing from the technical concept of the present disclosure. Therefore, the exemplary embodiments of the present disclosure are provided for illustrative purposes only and are not intended to limit the technical concept of the present disclosure. The protective scope of the present disclosure should be construed based on any appended claims and combinations thereof, and all the technical concepts in the equivalent scope thereof should be construed as falling within the scope of the present disclosure. As various changes could be made in the above methods and compositions without departing from the scope of the invention, it is intended that all matter contained in the above description shall be interpreted as illustrative and not in a limiting sense. Other embodiments within the scope of the claims herein will be apparent to one skilled in the art from consideration of the specification or practice of the exemplary embodiments disclosed herein. It is intended that the specification be considered exemplary only, with the scope and spirit of the described subject matter being indicated by the claims.

What is claimed is:

1. A regimen for the therapeutic treatment of rosacea, the regimen comprising topically applying to the skin of a subject in need of said treatment a pharmaceutical composition, the pharmaceutical composition comprising about 2.5% w/w to about 10% w/w benzoyl peroxide as an active ingredient, and a pharmaceutically acceptable carrier or excipient, wherein:
the benzoyl peroxide is the only active ingredient in said pharmaceutical composition;
the benzoyl peroxide is not encapsulated within a microcapsule or microsphere consisting of a metal oxide or a semi-metal oxide; and
said pharmaceutical composition comprises a fatty phase and/or an oily phase that forms a barrier between the benzoyl peroxide and its surrounding environment in the composition.

2. The regimen of claim 1, wherein said pharmaceutical composition comprises about 2.5% w/w to about 5% w/w of benzoyl peroxide.

3. The regimen of claim 1, wherein the benzoyl peroxide is not encapsulated within a microcapsule.

4. The regimen of claim 1, wherein after the topical application, skin irritation of the subject, and the amount of benzoic acid in the dermis of the skin of the subject, are decreased, compared to skin irritation of the subject and the amount of benzoic acid in the dermis of the skin of the subject, respectively, after topical application of a corresponding pharmaceutical composition without the fatty phase and/or the oily phase.

5. The regimen of claim 1, wherein an amount of benzoic acid in the stratum corneum and the epidermis of the skin of the subject after treatment with said pharmaceutical composition is higher than an amount of benzoic acid in the dermis of the skin of the subject after treatment with said pharmaceutical composition.

6. The regimen of claim 1, wherein the benzoyl peroxide is the sole active ingredient administered to the subject during the duration of the regimen.

7. The regimen of claim 1, wherein the pharmaceutical composition comprises about 5% w/w of benzoyl peroxide.

8. The regimen of claim 1, wherein the benzoyl peroxide is selected from a solid, solution or suspension form.

9. The regimen of claim 1, wherein the rosacea is any of erythematotelangiectatic rosacea, papulopustular rosacea, phymatous rosacea or ocular rosacea.

10. The regimen of claim 1, wherein said pharmaceutical composition is an extended-release formulation.

11. The regimen of claim 10, wherein the extended-release effect is obtained by encapsulation, microencapsulation, microspheres or coating.

12. The regimen of claim 1, wherein irritation observed on the skin of the subject after treatment with said pharmaceutical composition remains constant over time.

13. The regimen of claim 10, wherein the extended-release effect is obtained by the fatty phase and/or the oily phase that forms a barrier between the benzoyl peroxide and its surrounding environment in the composition.

14. The regimen of claim 1, wherein the benzoyl peroxide is not encapsulated within a microcapsule comprising an inorganic polymer.

15. The regimen of claim 1, wherein the pharmaceutical composition does not comprise a gelling agent.

16. The regimen of claim 1, wherein:
the fatty phase and/or the oily phase is dispersed in an aqueous phase; or
the pharmaceutical composition comprises an aqueous phase dispersed in the fatty phase and/or the oily phase.

17. The regimen of claim 1, wherein said pharmaceutical composition is a cream.

18. The regimen of claim 1, wherein the irritation is reduced when evaluated on a 0-3 scale.

19. A regimen for the therapeutic treatment of rosacea, the regimen comprising topically applying to the skin of a subject in need of said treatment a pharmaceutical composition, the pharmaceutical composition comprising about 2.5% w/w to about 10% w/w benzoyl peroxide as an active ingredient, and a pharmaceutically acceptable carrier or excipient, wherein the benzoyl peroxide is encapsulated within a microcapsule and is the only active ingredient in said pharmaceutical composition, wherein said pharmaceutical composition is a cream, and wherein an amount of benzoic acid in the stratum corneum and the epidermis of the skin of the subject after treatment with said pharmaceutical composition is higher than an amount of benzoic acid in the dermis of the skin of the subject after treatment with said pharmaceutical composition.

20. The regimen of claim 19, wherein the amount of benzoic acid in the stratum corneum and the epidermis of the skin of the subject is higher than the amount of benzoic acid in the dermis of the skin of the subject when measured by high-performance liquid chromatography (HPLC).

21. The regimen of claim 19, wherein the amount of benzoic acid in the stratum corneum and the epidermis of the skin of the subject is higher than the amount of benzoic acid in the dermis of the skin of the subject when measured by HPLC about 24 hours following the application of the pharmaceutical composition to the skin of the subject.

22. The regimen of claim 19, wherein the amount of benzoic acid in the stratum corneum and the epidermis of the skin of the subject is substantially higher than the amount of benzoic acid in the dermis of the skin of the subject after treatment with said pharmaceutical composition.

23. The regimen of claim 19, wherein irritation observed on the skin of the subject after treatment with said pharmaceutical composition is reduced compared to after treatment with a corresponding pharmaceutical composition in which the benzoyl peroxide is not encapsulated within a microcapsule.

24. The regimen of claim 23, wherein the irritation is reduced when evaluated on a 0-3 scale.

25. The regimen of claim 19, wherein the microcapsule comprises an inorganic polymer.

26. The regimen of claim 19, wherein the benzoyl peroxide is the sole active ingredient administered to the subject during the duration of the regimen.

27. The regimen of claim 19, wherein the pharmaceutical composition comprises about 5% w/w of benzoyl peroxide.

28. The regimen of claim 19, wherein the benzoyl peroxide is selected from a solid, solution or suspension form.

29. The regimen of claim 19, wherein the rosacea is any of erythematotelangiectatic rosacea, papulopustular rosacea, phymatous rosacea or ocular rosacea.

30. The regimen of claim 19, wherein said pharmaceutical composition is an extended-release formulation.

31. The regimen of claim 19, wherein the pharmaceutical composition does not comprise a gelling agent.

32. The regimen of claim 19, wherein irritation observed on the skin of the subject after treatment with said pharmaceutical composition remains constant over time.

33. A regimen for the therapeutic treatment of rosacea, the regimen comprising topically applying to the skin of a subject in need of said treatment a pharmaceutical composition, the pharmaceutical composition comprising about 2.5% w/w to about 10% w/w benzoyl peroxide as an active ingredient, and a pharmaceutically acceptable carrier or excipient, wherein the benzoyl peroxide is the only active ingredient in said pharmaceutical composition, wherein a total amount of benzoic acid in the skin of the subject after treatment with said pharmaceutical composition is less than about 18,333 ng/cm$^2$, and wherein said pharmaceutical composition is a cream.

34. The regimen of claim 33, wherein the amount of benzoic acid in the skin of the subject after treatment with said pharmaceutical composition ranges from about 6,667 ng/cm$^2$ to about 10,000 ng/cm$^2$.

35. The regimen of claim 33, wherein the amount of benzoic acid in the skin of the subject after treatment with said pharmaceutical composition ranges from about 7,500 ng/cm$^2$ to about 9,167 ng/cm$^2$.

36. The regimen of claim 33, wherein the benzoyl peroxide is not encapsulated within a microcapsule or a coating.

37. The regimen of claim 33, wherein the benzoyl peroxide is encapsulated within a microcapsule or a coating.

38. The regimen of claim 37, wherein the benzoyl peroxide is encapsulated within a microcapsule comprising an inorganic polymer.

39. The regimen of claim 33, wherein the benzoyl peroxide is the sole active ingredient administered to the subject during the duration of the regimen.

40. The regimen of claim 33, wherein the pharmaceutical composition comprises about 5% w/w of benzoyl peroxide.

41. The regimen of claim 33, wherein the benzoyl peroxide is selected from a solid, solution or suspension form.

42. The regimen of claim 33, wherein the rosacea is any of erythematotelangiectatic rosacea, papulopustular rosacea, phymatous rosacea or ocular rosacea.

43. The regimen of claim 33, wherein said pharmaceutical composition is an extended-release formulation.

44. The regimen of claim 33, wherein the pharmaceutical composition does not comprise a gelling agent.

45. The regimen of claim 33, wherein irritation observed on the skin of the subject after treatment with said pharmaceutical composition remains constant over time.

46. The regimen of claim 33, wherein irritation observed on the skin of the subject after treatment with said pharmaceutical composition is reduced compared to after treatment with a corresponding pharmaceutical composition that is not a cream.

47. The regimen of claim 46, wherein the irritation is reduced when evaluated on a 0-3 scale.

48. The regimen of claim 36, wherein irritation observed on the skin of the subject after treatment with said pharmaceutical composition is reduced compared to after treatment with a corresponding pharmaceutical composition that is not a cream.

49. The regimen of claim 48, wherein the irritation is reduced when evaluated on a 0-3 scale.

50. The regimen of claim 37, wherein irritation observed on the skin of the subject after treatment with said pharmaceutical composition is reduced compared to after treatment with a corresponding pharmaceutical composition that is not a cream.

51. The regimen of claim 50, wherein the irritation is reduced when evaluated on a 0-3 scale.

52. The regimen of claim 1, wherein the benzoyl peroxide is not encapsulated within a microcapsule or microsphere comprising a metal oxide or a semi-metal oxide.

* * * * *